United States Patent
Peng et al.

(10) Patent No.: US 10,844,319 B2
(45) Date of Patent: Nov. 24, 2020

(54) FATTY GLYCERIDE PREPARATION METHOD

(71) Applicant: Zhejiang Medicine Co., Ltd. Xinchang Pharmaceutical Factory, Xinchang County (CN)

(72) Inventors: Yongjian Peng, Xinchang County (CN); Xinde Xu, Xinchang County (CN); Shengnan Wang, Xinchang County (CN); Yuli Yu, Xinchang County (CN); Bin Shao, Xinchang County (CN)

(73) Assignee: ZHEJIANG MEDICINE CO., LTD. XINCHANG PHARMACEUTICAL FACTORY, Zhejiang (CN)

( * ) Notice: Subject to any disclaimer, the term of this patent is extended or adjusted under 35 U.S.C. 154(b) by 0 days.

(21) Appl. No.: 16/324,127

(22) PCT Filed: Aug. 1, 2017

(86) PCT No.: PCT/CN2017/095382
§ 371 (c)(1),
(2) Date: Mar. 15, 2019

(87) PCT Pub. No.: WO2018/028462
PCT Pub. Date: Feb. 15, 2018

(65) Prior Publication Data
US 2019/0256448 A1 Aug. 22, 2019

(30) Foreign Application Priority Data
Aug. 9, 2016 (CN) .......................... 2016 1 0646813

(51) Int. Cl.
| | |
|---|---|
| *C11C 3/06* | (2006.01) |
| *C07C 31/22* | (2006.01) |
| *C07C 67/03* | (2006.01) |
| *C11C 3/02* | (2006.01) |
| *C07C 69/604* | (2006.01) |

(52) U.S. Cl.
CPC .............. *C11C 3/06* (2013.01); *C07C 31/225* (2013.01); *C07C 67/03* (2013.01); *C07C 69/604* (2013.01); *C11C 3/02* (2013.01)

(58) Field of Classification Search
CPC .. C11C 3/02; C11C 3/06; C07C 67/03; C07C 31/225; C07C 69/24; C07C 69/28; C07C 69/30; C07C 69/587; C07C 69/604
See application file for complete search history.

(56) References Cited

U.S. PATENT DOCUMENTS

| | | | |
|---|---|---|---|
| 6,124,486 A | 9/2000 | Cherwin | |
| 7,067,684 B2 | 6/2006 | Westfechtel | |
| 8,227,010 B2 * | 7/2012 | Kase | ..................... C12P 7/6418 426/417 |
| 2005/0176977 A1 * | 8/2005 | Horlacher | ............... C07C 67/03 554/126 |
| 2007/0148746 A1 * | 6/2007 | Schoerken | ............ C12P 7/6454 435/134 |
| 2014/0303388 A1 * | 10/2014 | Kumita | ................... C07C 67/03 554/173 |

FOREIGN PATENT DOCUMENTS

| | | | |
|---|---|---|---|
| CN | 101818176 A | 9/2010 | |
| CN | 103880672 A | 6/2014 | |
| CN | 104479883 A * | 4/2015 | ............. C07C 67/03 |

OTHER PUBLICATIONS

CN 104479883 (A), Shen Junping et al., Preparation method for fatty glyceride, 2015, English translation 6 pages (Year: 2015).*

* cited by examiner

*Primary Examiner* — Yate' K Cutliff
(74) *Attorney, Agent, or Firm* — Ashok Tankha; Lipton, Weinberger and Husick

(57) ABSTRACT

The present invention provides a fatty glyceride preparation method, comprising converting fatty acid short-chain alcohol ester into fatty glyceride basic mixture by sequentially carrying out a normal-pressure reaction and a vacuum reaction in the nitrogen condition in the temperature of 80° C. to 150° C.; and meanwhile adding a basic catalyst and glycerin or adding a basic catalyst and a glycerin derivative into the fatty acid short-chain alcohol ester, so as to implement a conversion from the fatty acid short-chain alcohol ester to the fatty glyceride. Conditions of the preparation method are relatively moderate, and the structure of the fatty acid is not damaged in the reactions; the yield of the glyceride is high, compositions of the glyceride are stable and controllable, glyceride products having a high content of triacylglycerol can be obtained; the process is simple, costs are low, and the fatty glyceride is applicable to industrial production.

5 Claims, No Drawings

FATTY GLYCERIDE PREPARATION METHOD

CROSS-REFERENCE TO RELATED APPLICATIONS

This application is a national phase application of PCT application no. PCT/CN2017/095382, titled "Fatty Glyceride Preparation Method", filed on Aug. 1, 2017 which claims priority to and the benefit of the non-provisional patent application titled "Fatty Glyceride Preparation Method", application number 201610646813.7, filed in the Chinese Patent Office on Aug. 9, 2016. The specifications of the above referenced patent applications are incorporated herein by reference in their entirety

FIELD OF THE INVENTION

The present invention relates to a fatty glyceride preparation method. In comparison with free fatty acids, fatty acid methyl esters and fatty acid ethyl esters, a fatty glyceride has no pungent smell and stable in storage, has the same configuration as natural plant oil and is easier to absorb by human body.

BACKGROUND OF THE INVENTION

Content of fatty acids is relatively fixed in natural animal and plant oils. Especially, content of some essential fatty acids such as linoleic acid, linolenic acid, DHA and EPA with bioactivity are too low to apply in the fields of medicine and health products. These components in the form of glyceride are difficult to purify. Glyceride is firstly converted into fatty acid short-chain alcohol ester and then crystallized, distilled, and extracted to increase contents of related components in order to increase the content of functional fatty acid. Content of a target component in the purified fatty acid short-chain alcohol ester is high. But these short-chain alcohol esters has no natural configuration and has these deficiencies such as instability in storage, pungent smell and low human absorptivity, and can not completely embody active advantages of high-content functional fatty acids. Thus these short-chain alcohol esters need to be converted into natural configuration (i.e. a glyceride form) having a high human absorptivity, good oxidation stability and mild smell and taste. These converted functional fatty acids can be better applied for the fields of medicines, health products and dietary supplements.

Currently, methods for preparing a glyceride comprise an enzymic method and a chemical method. An enzymic method has advantages of moderate process conditions, green non-pollution. Chinese patent publication No. CN 103880672A utilizes an enzymic catalysis method to convert purified algal oil DHA ethyl ester into DHA glyceride. Likewise, Chinese patent application No. CN201010147162.X utilizes an enzymic catalysis method to prepare glyceride by reacting a fatty acid ethyl ester with glycerol in order to convert functional fatty acids such as ethyl ester type fish oil, algal oil, conjugated linoleic acid, and arachidonic acid can be converted into glyceride. However, it can be seen from these embodiments of the above-mentioned patents that enzyme costs of these methods are relatively high, and enzyme activities are influenced by various factors such as equipment, temperature and material composition and vacuum condition. In addition, the reaction period is relatively long, the production efficiency is low. These factors limit the application in industrial production.

A method for preparing a glyceride by a chemical method comprises reacting fatty acid or derivative thereof with glycerol or derivative thereof under catalysis of a chemical catalyst. U.S. Pat. No. 6,124,486 utilizes fatty acid reacting with glycerol triacetate to prepare glycerides by fatty acid soap catalysis, wherein the method requires a temperature of 200-260° C. But the double-bond configuration of some polyunsaturated fatty acids such as linolenic acid and DHA can be changed at a temperature, and even produces cracking of fatty acid, so that qualities and yields of products are adversely affected. U.S. Pat. No. 7,067,684 discloses a method for preparing a conjugated linoleic acid glyceride, by carrying out ester exchange reaction by reacting a lower alcohol ester of conjugated linoleic acid with glycerin triacetate. In comparison with the reaction of fatty acid and glycerol, the process can obviously reduce required temperature of no more than 150° C. and has less damage to the structure of fatty acids especially polyunsaturated fatty acids. However, please note that the boiling point of glycerol or derivative thereof is relatively low under vacuum condition, for example, the boiling point of glycerol is 125.5° C. while the boiling point of glycerol triacetate is merely 100° C. under a vacuum degree 133 pa. So quite a part of glycerol or derivative thereof can be distilled and extracted in a direct high-temperature reaction under vacuum condition. It certainly causes yields of products lower. Moreover, the product quality is influenced due to changes of material composition of the reaction system, and ratios of triglyceride, diglyceride and monoglyceride in products is also unstable. In particular, contents of triglyceride in products is relatively low. Announcement No. 12 of 2009 of the National Health Commission of the People's Republic of China approved that a conjugated linoleic acid glyceride is a new resource food. Their quality requirements for conjugated linoleic acid glyceride have been stipulated in detail and the content of triglyceride in products is required to be 77-83%, and the content of triglyceride prepared by this process is relatively low and can not meet the standard requirements.

On the whole, there are certain deficiencies in the process of preparing a fatty glyceride at present. An enzymic catalysis method has high cost, long reaction cycle and high requirements for process equipments. And consequently it is difficult to industrialize production. A chemical method requires high temperature. Consequently it is adverse to structural stability of polyunsaturated fatty acids. In addition, the boiling point of glycerin or derivative thereof is relatively low under vacuum condition, and glycerol or derivative thereof can be distilled and extracted during direct high-temperature reaction under vacuum condition. On one hand, it causes yields of glyceride low. On the other hand, it also causes ratios of triglyceride, diglyceride and monoglyceride of products unstable. In particular, the content of triglyceride of products is relatively low. These would directly affect the quality of products.

SUMMARY OF THE INVENTION

The technical problem to be solved by the present invention is to overcome the deficienciess of the prior art and to provide a method for preparing a fatty glyceride. The method of the present invention has low cost, short reaction period, no damage to the composition of fatty acids during reaction process, and high yield of glyceride. The composition of products is stable and controllable. In particular, products having a high-content of triglyceride can be obtained. The method has low cost, short reaction period, non-damaged structure of the fatty acid in the reactions, high yield of the glyceride, stable and controllable glyceride compositions, especially high content of triacylglycerol obtained.

The technical problem to be solved by the present invention is to provide a fatty glyceride preparation method, comprising converting fatty acid short-chain alcohol ester into fatty glyceride basic mixture by sequentially carrying out a normal-pressure reaction and a vacuum reaction in nitrogen condition in a temperature of 80° C. to 150° C., to convert to a fatty glyceride basic mixture; and meanwhile adding a basic catalyst and glycerin or adding a basic catalyst and a glycerin derivative into the fatty acid short-chain alcohol ester, so as to implement a conversion from the fatty acid short-chain alcohol ester to the fatty glyceride.

In the preferable technical solution of the present invention, preferably, the fatty acid short-chain alcohol ester is C16-C22 fatty acid methyl ester or C16-C22 fatty acid ethyl ester.

In the preferable technical solution of the invention, preferably, the vacuum degree in the vacuum reaction is 50-10000 Pa.

In the preferable technical solution of the invention, preferably, adding an acid water into the fatty glyceride basic mixture, and washing an oil layer by water to pH=6-7 to obtain crude glyceride.

In the preferable technical solution of the invention, preferably, the acid water is selected from the group consisting of phosphoric acid aqueous solution, acetic acid aqueous solution, and citric acid aqueous solution.

In the preferable technical solution of the invention, preferably, the acid water has a concentration of 0.2-1.5 mol/L.

In the preferable technical solution of the invention, preferably, decolorizing and then distilling the crude glyceride to obtain a fatty acid glyceride product.

In the preferable technical solution of the invention, preferably, the basic catalyst is potassium alkoxide or sodium alkoxide, the glycerol derivative is an ester formed by a C1-C3 short-chain acid.

In the preferable technical solution of the invention, preferably, the potassium alkoxide is potassium methoxide or potassium ethoxide; the sodium alkoxide is sodium methoxide or sodium ethoxide.

In the preferable technical solution of the invention, preferably, a content of triglyceride in the fatty acid glyceride product is more than 80%.

Given the problems with the prior art, the present invention prepares a fatty glyceride by a chemical method. In particular, a fatty acid methyl ester or fatty ethyl ester as a raw material reacts with glycerol or an ester formed by glycerol and C1-C3 short-chain acid under vacuum condition. In comparison with direct reaction of fatty acid with glycerol, the method of the present invention can greatly reduce the reaction temperature and prevent from damaging the structure of fatty acid in the reaction process. In the meantime, glycerol or derivative thereof is converted into monoglyceride or diglyceride by carrying out a normal-pressure reaction under nitrogen environment at the initial stage of the reaction. It greatly increases the boiling point of the reactant. And then a vacuum reaction is carried out. It not only removes reactants with low boiling point in the reaction process to make the equilibrium go in the positive direction, but also effectively prevents from distillation loss of reactants such as glycerol and derivative thereof with low boiling point at high temperature under vacuum condition. It remarkably improves yields of glyceride, and makes the composition of triglyceride, diglyceride and monoglyceride of products more stable and controllable.

The present invention has advantages as follows: conditions of the preparation method are relatively moderate, and the structure of the fatty acid is not damaged in the reactions; the yield of the glyceride is high, compositions of the glyceride are stable and controllable, glyceride products having a high content of triacylglycerol can be obtained; the process is simple, costs are low, and the fatty glyceride is applicable to industrial production.

DETAILED DESCRIPTION OF THE INVENTION

Hereafter, the present invention will be described specifically with reference to the examples. The examples are given only for illustration of the technical solution of the present invention and should not be construed to limit the present invention.

Example 1

To add 100 g of a purified palmitic acid (C16:0) methyl ester to 11 g of glycerol to obtain a mixture, and then heat the mixture to 80° C., afterwards dropwise add 1 mL of sodium methoxide solution to carry out a normal-pressure reaction under nitrogen condition at a temperature of 80° C. for 1 h, and open the vacuum and continue to carry out a reaction under a pressure of 50 Pa for 2 h to obtain a fatty glyceride basic mixture.

To add 100 ml of water and 1.2 g of acetic acid into the fatty glyceride basic mixture and carry out a neutralization reaction under stirring and keeping warm for 5 minutes, and then let stand for layered, remove a water layer, and wash a grease layer by water to pH=6-7, remove water by vacuum rotary steam to obtain a crude palmitic acid glyceride.

To carry out a molecular distillation of the crude palmitic acid glyceride after decoloration of the crude palmitic acid glyceride, to remove unreacted impurities such as methyl ester to obtain a product with high content of palmitic acid glyceride, and the yield of palmitic acid glyceride in the product is 95.1%, the content of triglyceride is 80.8%, and the content of palmitic acid in the product is 90.6%.

Example 2

To add 200 g of a purified linolenic acid (C18:3) methyl ester to 50 g of glycerol triacetate to obtain a mixture, and then heat the mixture to 120° C., afterwards dropwise add 4 mL of sodium methoxide solution to carry out a normal-pressure reaction under nitrogen condition at a temperature of 120° C. for 1 h, and open the vacuum and continue to carry out a reaction under a pressure of 1000 Pa for 3 h to obtain a linolenic acid glyceride basic mixture.

To add 200 ml of water and 4 g of phosphoric acid into the linolenic acid glyceride basic mixture and carry out a neutralization reaction under stirring and keeping warm for 10 minutes, and then let stand for layered, remove a water layer, and wash a grease layer by water to pH=6-7, remove water by vacuum rotary steam to obtain a crude linolenic acid glyceride.

To carry out a molecular distillation of the crude linolenic acid glyceride after decoloration of the crude linolenic acid glyceride, to remove unreacted impurities such as methyl ester to obtain a product with high content of linolenic acid glyceride, and the yield of linolenic acid glyceride in the product is 94.5%, the content of triglyceride is 83.6%, and the content of linolenic acid in the product is 81.2%.

Example 3

To add 200 g of a purified conjugated linoleic acid (C18:2) ethyl ester to 38 g of glycerin triformate (that is, triformin) to obtain a mixture, and then heat the mixture to 90° C., afterwards dropwise add 2 mL of sodium ethoxide solution to carry out a normal-pressure reaction under nitrogen condition at a temperature of 90° C. for 2 h, and open the vacuum and continue to carry out a reaction under a pressure of 10000 Pa for 3 h to obtain a conjugated linoleic acid glyceride basic mixture.

To add 100 ml of water and 5 g of citric acid into the conjugated linoleic acid glyceride basic mixture and carry out a neutralization reaction under stirring and keeping warm for 5 minutes, and then let stand for layered, remove a water layer, and wash a grease layer by water to pH=6-7, remove water by vacuum rotary steam to obtain a crude conjugated linoleic acid glyceride.

To carry out a molecular distillation of the crude conjugated linoleic acid glyceride after decoloration of the crude conjugated linoleic acid glyceride, to remove unreacted impurities such as ethyl ester to obtain a product with high content of conjugated linoleic acid glyceride, and the yield of conjugated linoleic acid glyceride in the product is 95.5%, the content of triglyceride is 81.3%, and the content of conjugated linoleic acid in the product is 80.5%.

Example 4

To add 500 g of a purified algal oil DHA (C22:6) ethyl ester to 124 g of glycerol tripropionate to obtain a mixture, and then heat the mixture to 100° C., afterwards dropwise add 10 mL of sodium ethoxide solution to carry out a normal-pressure reaction under nitrogen condition at a temperature of 150° C. for 1 h, and open the vacuum and continue to carry out a reaction under a pressure of 5000 Pa for 3 h to obtain an algal oil DHA glyceride basic mixture.

To add 100 ml of water and 8 g of acetic acid into the algal oil DHA glyceride basic mixture and carry out a neutralization reaction under stirring and keeping warm for 10 minutes, and then let stand for layered, remove a water layer, and wash a grease layer by water to pH=6-7, remove water by vacuum rotary steam to obtain a crude algal oil DHA glyceride.

To carry out a molecular distillation of the crude algal oil DHA glyceride after decoloration of the crude algal oil DHA glyceride, to remove unreacted impurities such as ethyl ester to obtain a product with high content of algal oil DHA glyceride, and the yield of algal oil DHA glyceride in the product is 92.1%, the content of triglyceride is 86.2%, and the content of DHA in the product is 72.3%.

Example 5

The product of fatty glycerides obtained by Examples 1-4 are prepared for corresponding methyl ester or ethyl ester by alcoholysis. The content of a target component is determined by GC. The content after the reaction relative to the content before the reaction are shown in Table 1.

TABLE 1

| The target component and its content | Example 1 (C16:0) | Example 2 (C18:3) | Example 3 (C18:2) | Example 4 (C22:6) |
| --- | --- | --- | --- | --- |
| Before the reaction | 90.5% | 81.2% | 80.8% | 72.7% |
| After the reaction | 90.6% | 81.2% | 80.5% | 72.3% |

It may be seen from the comparison of Table 1 that no content change of the target component before the reaction and after the reaction is obviously occurred. The process is suitable for both saturated fatty acids without double bonds and unsaturated fatty acids with multiple double bonds.

Example 6

Control experiments of Examples 1-4 are carried out. The reactions of the control experiments are directly reacted under vacuum condition without previous normal-pressure reaction, and other process parameters are the same as the examples 1-4. In comparison with the yield of the fatty glyceride and the content of triglyceride of the control groups and the examples 1-4, the results are shown in Table 2.

TABLE 2

| Results | Example 1 | Control group 1 | Example 2 | Control group 2 | Example 3 | Control group 3 | Example 4 | Control group 4 |
| --- | --- | --- | --- | --- | --- | --- | --- | --- |
| yield of glyceride % | 95.1 | 87.9 | 94.5 | 80.1 | 95.5 | 85.6 | 92.1 | 69.1 |
| content of triglyceride % | 80.8 | 78.0 | 83.6 | 75.2 | 81.3 | 79.1 | 86.2 | 73.4 |

Compared with the examples 1-4 of the preset invention, both of the yield of glyceride and the content of triglyceride of the control groups are relatively low. Especially, the differences between the examples 1-4 and the control groups are more significant in the case of higher reaction temperature. The process of the present invention can significantly increase the yield of glyceride and the content of triglyceride.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

We claim:

1. A fatty glyceride preparation method, comprising:

converting fatty acid short-chain alcohol ester into fatty glyceride basic mixture by in sequence carrying out a normal-pressure reaction and a vacuum reaction in nitrogen condition at a temperature of 80° C. to 150° C., and meanwhile adding a basic catalyst and a glycerin derivative into the fatty acid short-chain alcohol ester, so as to implement a conversion from the fatty acid short-chain alcohol ester to the fatty glyceride, wherein the basic catalyst is potassium alkoxide or sodium alkoxide, wherein the glycerol derivative is glycerol triacetate, glycerin triformate, or glycerol tripropionate;

adding an acid water into the fatty glyceride basic mixture, wherein the acid water is selected from the group consisting of phosphoric acid aqueous solution, acetic acid aqueous solution, and citric acid aqueous solution;

washing an oil layer by water to pH=6-7 to obtain crude glyceride; and sequentially decolorizing and distilling the crude fatty acid glyceride to obtain the fatty acid glyceride product, wherein a content of triglyceride in the fatty acid glyceride product is more than 80%.

2. The fatty glyceride preparation method according to claim 1, wherein the fatty acid short-chain alcohol ester is C16-C22 fatty acid methyl ester or C16-C22 fatty acid ethyl ester.

3. The fatty glyceride preparation method according to claim 1, wherein a vacuum degree in the vacuum reaction is 50-10000 Pa.

4. The fatty glyceride preparation method according to claim 1, wherein the acid water has a concentration of 0.2-1.5 mol/L.

5. The fatty glyceride preparation method according to claim 1, wherein the potassium alkoxide is potassium methoxide or potassium ethoxide, and wherein the sodium alkoxide is sodium methoxide or sodium ethoxide.

* * * * *